United States Patent
Farley et al.

(10) Patent No.: US 9,814,793 B2
(45) Date of Patent: Nov. 14, 2017

(54) STAGED DRY OUT CONTROL FOR EVAPORATIVE MEDIA SYSTEMS

(71) Applicant: DRI-STEEM Corporation, Eden Prairie, MN (US)

(72) Inventors: Cole K. Farley, Long Lake, MN (US); Mark Allen Kirkwold, Shakopee, MN (US); James M. Lundgreen, Lakeville, MN (US)

(73) Assignee: DI-STEEM Corporation, Eden Prairie, MN (US)

( * ) Notice: Subject to any disclaimer, the term of this patent is extended or adjusted under 35 U.S.C. 154(b) by 484 days.

(21) Appl. No.: 14/599,035

(22) Filed: Jan. 16, 2015

(65) Prior Publication Data

US 2015/0204554 A1 Jul. 23, 2015

Related U.S. Application Data

(60) Provisional application No. 61/928,800, filed on Jan. 17, 2014, provisional application No. 61/928,740, (Continued)

(51) Int. Cl.
*F28C 3/08* (2006.01)
*A61L 2/10* (2006.01)
(Continued)

(52) U.S. Cl.
CPC ............ *A61L 2/10* (2013.01); *B01F 3/04021* (2013.01); *B01F 3/04078* (2013.01); *B01F 3/04085* (2013.01); *F24F 5/0035* (2013.01); *F24F 6/043* (2013.01); *F25B 39/02* (2013.01); *F25B 39/028* (2013.01); *F25D 7/00* (2013.01); *F28C 3/08* (2013.01); *G05D 9/12* (2013.01);
(Continued)

(58) Field of Classification Search
CPC .. F24F 5/0035; F24F 5/043; F24F 2001/0088; B01F 3/04021; B01F 3/04078; Y02B 30/545; F25D 7/00; F28C 3/08
USPC .................................. 62/121, 171, 259.4
See application file for complete search history.

(56) References Cited

U.S. PATENT DOCUMENTS 2,160,549 A 5/1939 Kurth
6,078,729 A 6/2000 Kopel
(Continued)

FOREIGN PATENT DOCUMENTS

WO   WO 01/79771 A1   10/2001
WO   WO 2007/055838 A2   5/2007

*Primary Examiner* — Frantz Jules
*Assistant Examiner* — Meraj A Shaikh
(74) *Attorney, Agent, or Firm* — Merchant & Gould P.C.

(57) ABSTRACT

A staged dry out process and control system for an evaporative media cooling system having a plurality of media stages that are selectively activated and deactivated by a control system is disclosed. The staged dry out process ensures that wet media stages are appropriately dried with minimal disruption to the staging strategy implemented by the control system. In one aspect, the staged dry out process monitors deactivated media stages to determine if the media stages reach a dry state before being activated. In another aspect, the staged dry out process locks out a media stage that has been in a wet state beyond a predetermined maximum time limit until the media stage attains a dry state. With this strategy the cooling system can operate without being required to completely shut down for a drying process.

20 Claims, 4 Drawing Sheets

Related U.S. Application Data filed on Jan. 17, 2014, provisional application No. 61/928,764, filed on Jan. 17, 2014, provisional application No. 61/928,775, filed on Jan. 17, 2014, provisional application No. 61/928,784, filed on Jan. 17, 2014.

(51) Int. Cl.
<table>
<tr><td>F24F 5/00</td><td>(2006.01)</td></tr>
<tr><td>B01F 3/04</td><td>(2006.01)</td></tr>
<tr><td>F25B 39/02</td><td>(2006.01)</td></tr>
<tr><td>F25D 7/00</td><td>(2006.01)</td></tr>
<tr><td>G05D 9/12</td><td>(2006.01)</td></tr>
<tr><td>F24F 6/04</td><td>(2006.01)</td></tr>
<tr><td>F24F 1/00</td><td>(2011.01)</td></tr>
</table>

(52) U.S. Cl.
CPC ..... *F24F 2001/0088* (2013.01); *Y02B 30/545* (2013.01); *Y10T 137/0318* (2015.04); *Y10T 137/7303* (2015.04)

(56) References Cited

U.S. PATENT DOCUMENTS

| | | | |
|---|---|---|---|
| 6,338,471 B1 | 1/2002 | Imsdahl et al. | |
| 6,513,339 B1 | 2/2003 | Kopko | |
| 7,165,410 B2 | 1/2007 | Carr et al. | |
| 7,712,300 B2* | 5/2010 | Bevilacqua | F02C 1/05 60/39.53 |
| 7,744,068 B2* | 6/2010 | Lundgreen | F24F 6/18 261/115 |
| 7,765,827 B2 | 8/2010 | Schlom et al. | |
| 8,496,732 B2 | 7/2013 | Culp et al. | |
| 8,534,644 B2* | 9/2013 | Lundgreen | F24F 6/18 239/600 |
| 8,534,645 B2* | 9/2013 | Lundgreen | F24F 6/18 261/115 |
| 9,603,957 B2* | 3/2017 | Kirkwold | A61L 2/10 |
| 9,675,719 B2* | 6/2017 | Kirkwold | A61L 2/10 |
| 2001/0054354 A1 | 12/2001 | Baudat et al. | |
| 2004/0093882 A1* | 5/2004 | Sangwan | B60H 1/00885 62/244 |
| 2005/0166615 A1 | 8/2005 | Carr et al. | |
| 2007/0101746 A1* | 5/2007 | Schlom | F24F 5/0007 62/310 |
| 2011/0030552 A1* | 2/2011 | Fong | F01K 25/06 92/144 |
| 2012/0118148 A1 | 5/2012 | Culp et al. | |
| 2012/0118155 A1* | 5/2012 | Claridge | B01D 53/268 96/9 |
| 2013/0333407 A1* | 12/2013 | Jarvis | F28C 3/08 62/314 |
| 2014/0190198 A1* | 7/2014 | Slessman | H05K 7/20836 62/314 |
| 2015/0204552 A1 | 7/2015 | Kirkwold et al. | |
| 2015/0204553 A1 | 7/2015 | Kirkwold et al. | |
| 2015/0204588 A1 | 7/2015 | Lundgreen et al. | |
| 2015/0205305 A1* | 7/2015 | Kirkwold | B01F 3/04078 137/1 |
| 2015/0260419 A1 | 9/2015 | Muenzberg et al. | |

\* cited by examiner

STAGED DRY OUT CONTROL FOR EVAPORATIVE MEDIA SYSTEMS

CROSS REFERENCE TO RELATED APPLICATIONS

This application claims priority to U.S. Application Ser. No. 61/928,740, filed on Jan. 17, 2014, entitled "Evaporative Cycles of Concentration Control," the entirety of which is incorporated by reference herein. This application also claims priority to U.S. Application Ser. No. 61/928,764, filed on Jan. 17, 2014, entitled "Circulation and Drain System," the entirety of which is incorporated by reference herein. This application claims priority to U.S. Application Ser. No. 61/928,775 filed on Jan. 17, 2014, entitled "Staging Control for an Evaporative Media System," the entirety of which is incorporated by reference herein. This application also claims priority to U.S. Application Ser. No. 61/928,784, filed on Jan. 17, 2014, entitled "Staging Control for an Evaporative Media System," the entirety of which is incorporated by reference herein. This application also claims priority to U.S. Application Ser. No. 61/928,800, filed on Jan. 17, 2014, entitled "Staged Dry Out Control for Evaporative Media Systems," the entirety of which is incorporated by reference herein.

BACKGROUND

Evaporative media systems, for example direct evaporative coolers, are frequently used in commercial and industrial HVAC systems, including applications for data centers and power plant turbine inlet cooling. Evaporative media systems consume less energy than conventional cooling equipment and are increasingly being used to supplement and occasionally replace conventional cooling equipment. In operation, evaporative media systems use the enthalpy of vaporization of water as a means to cool and humidify air. Typically, this is accomplished by flowing air directly through a media wetted with water. As air passes through the wetted media, water evaporates by taking energy from the air to vaporize the water. Accordingly, the air temperature exiting the wetted media is reduced and the humidity is increased while the energy or enthalpy of the exiting air remains the same as the entering air. This type of a process is often referred to as adiabatic cooling.

Evaporative media systems typically use a water pump to transfer water in a tank below the media to the top of the media. The water flows down through the media where a small portion of the water evaporates and a relatively larger portion drains out the media bottom into the tank below. The water continues to be recirculated using the water pump, or re-circulation pump, with make-up water added to replace the evaporated water. Tank water is periodically drained and replaced with additional make-up water to control tank water concentration and minimize scale fouling, biological fouling and corrosion.

The air flowing through an evaporative media system allows for the introduction of algae. Additionally, the continuously wet environment may allow that algae to propagate. If measures are not taken, algae can fowl the media and contaminate the air being conditioned by the system. To prevent the continuous growth of algae, it is common practice to allow the media to completely dry out at least once in any given 24 hour period in a dry out cycle. However, by requiring the media in an evaporative media system to completely dry out, the system is necessarily inactive and no longer flowing water. Thus, the desired cooling and humidification effects are temporarily lost during the dry out cycle. The length of a dry out cycle, and subsequent delay in desired output, is dependent on incoming air conditions. The dry out cycle is often a scheduled event that occurs regardless of past system output. Improvements are desired.

SUMMARY

A staged dry out process and control system for an evaporative media cooling system having a plurality of media stages that are selectively activated and deactivated by a control system is disclosed. One step of the process includes monitoring the condition of each media stage to determine whether the media stage is in a wet state or a dry state while another step includes starting a wet condition timer for each stage that is in a wet state. In one step, each media stage is monitored as being activated or deactivated by the control system. For any deactivated media stage, the process can include assigning a demand based drying status to the media stage as long as the media stage is in a wet state and assigning a dry status to the media stage if or when the media stage reaches a dry state. For any activated media stage that has not been in a wet state for greater than a maximum predefined time period, the process may include assigning a wet status to the media stage. For any activated media stage that has been in a wet state for greater than a maximum predefined time period, the process may include locking out the media stage from activation by the control system until the media stage has reached a dry state and then assigning a dry status to the media stage. In one embodiment, the maximum predefined time period is 24 hours. In one embodiment, the control system is a demand based control algorithm that activates and deactivates the media stages as necessary to satisfy a cooling demand. In one embodiment, only one media stage is allowed to be locked out at any given time to ensure that the evaporative media cooling system can stage or activate all remaining stages that might be needed to satisfy the cooling demand.

DESCRIPTION OF THE DRAWINGS

Non-limiting and non-exhaustive embodiments are described with reference to the following figures, which are not necessarily drawn to scale, wherein like reference numerals refer to like parts throughout the various views unless otherwise specified.

DETAILED DESCRIPTION

Figure 1:
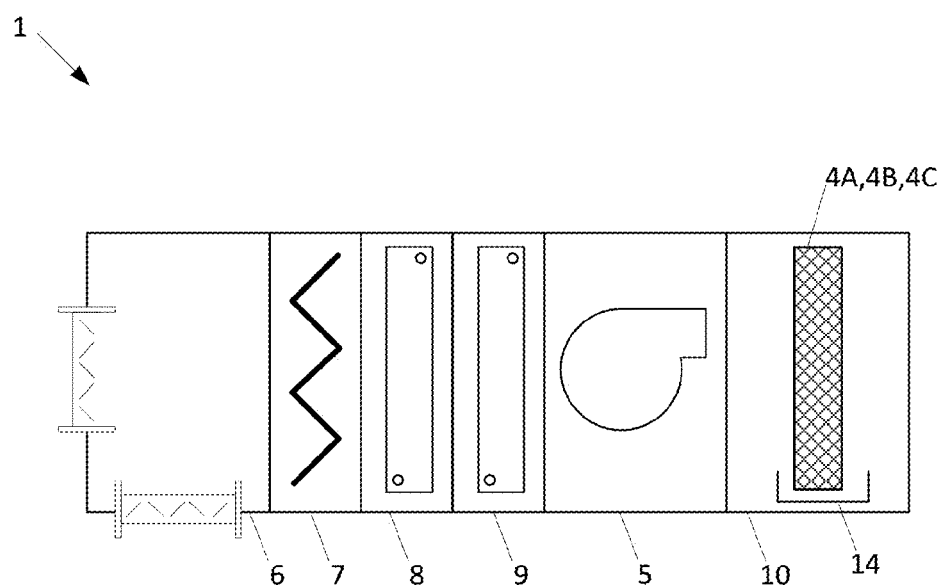
FIG. 1 is a schematic side view of an air handling system having features that are examples of aspects in accordance with the principles of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

General Evaporative Media System Description

Figure 2:
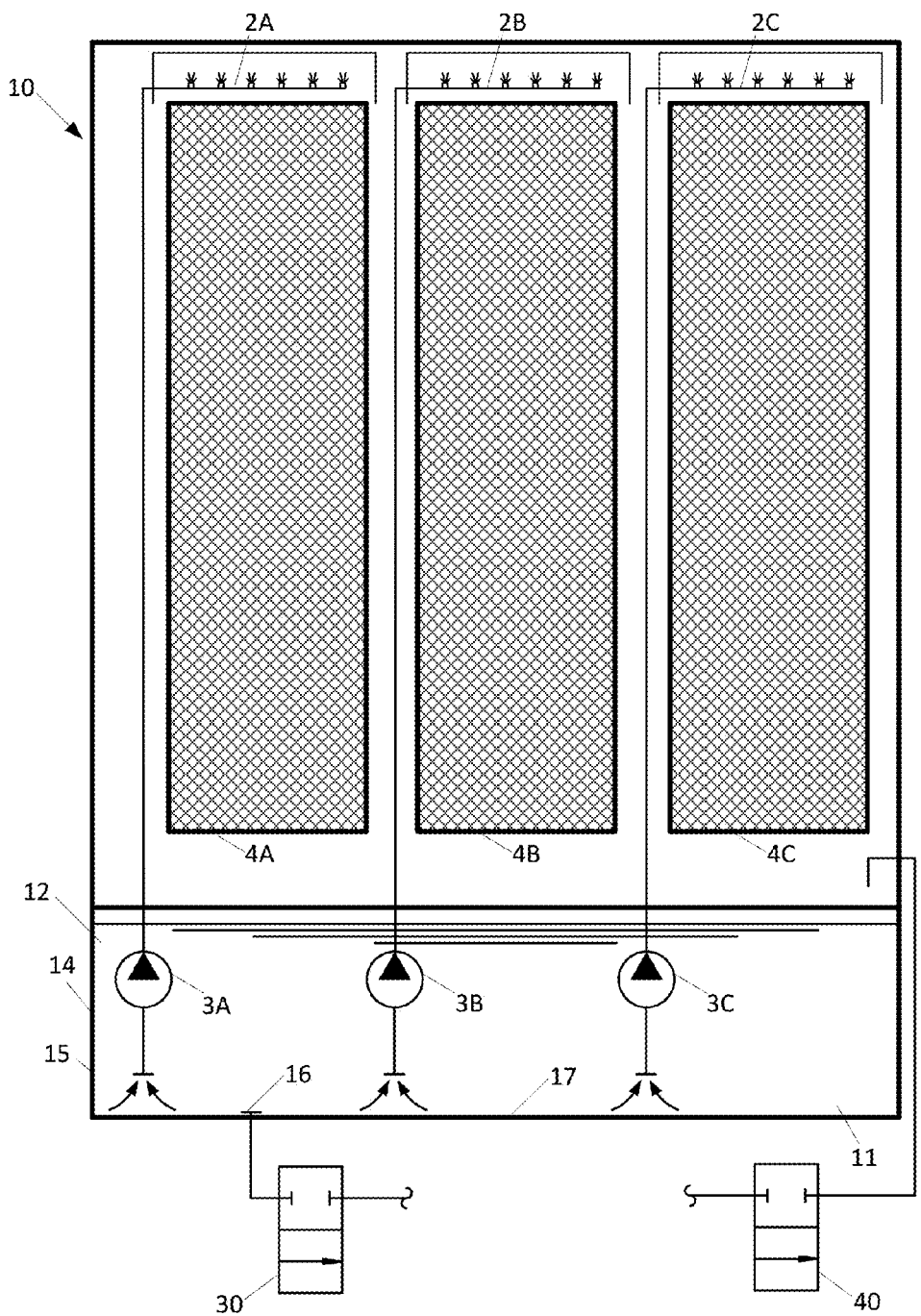
FIG. 2 is a schematic end view of a three stage evaporative media system having features that are examples of aspects in accordance with the principles of the present disclosure, the evaporative media system being usable in the air handling system shown in FIG. 1.
Figure 3:
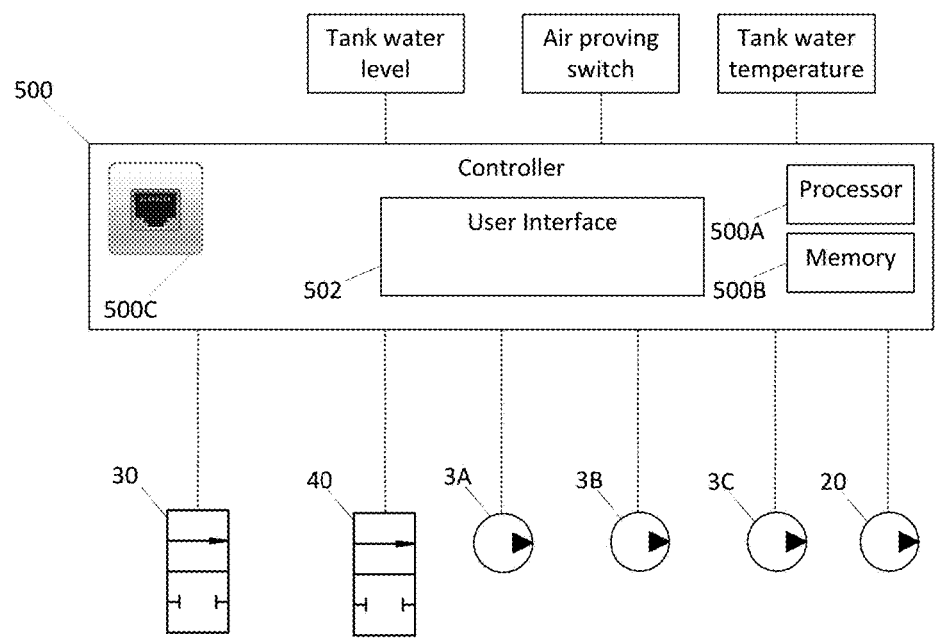
FIG. 3 is a schematic view of a control system usable with the evaporative media system shown in FIG. 1.

Referring to FIG. 1, an air handling system 1 comprising an evaporative media system 10 is shown. FIG. 2 shows a three stage version of the evaporative media system 10 in additional detail. As shown, the air handling unit may be additionally provided with a supply fan 5, a damper section 6, a filter 7, a heating coil 8, and a cooling coil 9. It should be understood that various other components and alternative configurations may be applied to air handling system 1 without departing from the concepts disclosed herein. In operation, the supply fan 5 draws air through the evaporative media system 10 to result in adiabatically cooled air when the evaporative media system 10 is activated.

In one aspect, the evaporative media system 10 shown at FIG. 2 includes an evaporator tank 14 having a sidewall 15 and a bottom side 17 that together define an interior volume 11 for holding a fluid 12, such as water. As shown, the tank 14 defines a single compartment with a single interior volume 11 for holding a fluid 12. The sidewall 15 may have various cross-sectional shapes as dictated by the requirements of the evaporator and air handling unit, for example square, rectangular, and circular cross-sectional shapes. The bottom side 17 may also be provided with various shapes to accommodate the perimeter defined by the sidewall 15.

The storage tank 14 may be provided with a drain opening 16 located in one of the bottom side 17 and the sidewall 15. In the particular embodiment shown, the drain opening 16 is provided at the bottom side 17 of the tank 14. In one aspect, a drain valve 30 is provided to selectively drain water from the tank 14 while a fill valve 40 is provided to selectively add water to the tank 14. The drain and fill valves 30, 40 may be provided as automatic control valves operated by a controller, such as electronic controller 500 discussed below.

As presented, evaporative media system 10 also includes a plurality of media stages 4A, 4B, 4C through which air is drawn via the operation of fan 5. FIG. 2 shows a three stage system having stages 4A, 4B, 4C of a generally equal size and capacity. It should be appreciated that the evaporative media system 10 may include fewer or more media stages of same or different sizes without departing from the concepts disclosed herein. Furthermore, each media stage may include multiple subsections of media. As shown, each media section 4A, 4B, 4C is separated from the other by a gap, or alternatively a frame or barrier to prevent moisture from communicating from one section to the other. This configuration allows for an individual media section to be dry out without being subjected to wicking moisture from an adjacent section.

Each individual media stage 4A, 4B, 4C is shown as being provided with an individual corresponding distribution pump 3A, 3B, 3C. A spray distribution apparatus 2A, 2B, 2C is in fluid communication with each pump 3A, 3B, 3C such that each pump 3A, 3B, 3C can deliver fluid 12, such as water, from the storage tank 14 to a spray distribution apparatus 2A, 2B, 2C to wet the associated media stage 4A, 4B, 4C. One suitable pump for pumps 3A, 3B, and 3C is a Little Giant F-Series F10-1200 (manufactured by Franklin Electric of Oklahoma City, Okla.). This type of pump has a wet rotor design without a shaft seal to separate the motor from the pump wherein water circulates around the armature.

In operation, when a pump 3A, 3B, 3C is activated (e.g. turned on or modulated to a speed greater than zero), the associated media stage 4A, 4B, 4C is wetted with fluid 12. When a media stage 4A, 4B, 4C is being actively wetted with water, for example when the associated pump 3A, 3B, 3C is in operation, that media stage 4A, 4B, 4C can be referred to as being activated. Likewise, when a media stage 4A, 4B, 4C is not being actively wetted with water, for example when the associated pump 3A, 3B, 3C is shut off and not in operation, that media stage 4A, 4B, 4C can be referred to as being deactivated.

Control System

Referring to FIG. 2, the evaporative media system may also include an electronic controller 500. The electronic controller 500 is schematically shown as including a processor 500A and a non-transient storage medium or memory 500B, such as RAM, flash drive or a hard drive. Memory 500B is for storing executable code, the operating parameters, and the input from the operator user interface 502 while processor 500A is for executing the code. The electronic controller is also shown as including a transmitting/receiving port 500C, such as an Ethernet port for two-way communication with a WAN/LAN related to an automation system. A user interface 502 may be provided to activate and deactivate the system, allow a user to manipulate certain settings or inputs to the controller 500, and to view information about the system operation.

The electronic controller 500 typically includes at least some form of memory 500B. Examples of memory 500B include computer readable media. Computer readable media includes any available media that can be accessed by the processor 500A. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the processor 500A.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Electronic controller 500 is also shown as having a number of inputs/outputs that may be used for implementing desired operational modes of the evaporative media system 10 and/or the air handling system 1. For example, electronic controller 500 provides outputs for commanding individual evaporator stage pumps 3A, 3B, 3C such that they can be staged as needed to meet the output demands of the system 10 (e.g. a leaving air temperature or relative humidity set point). Controller 500 may also provide outputs for controlling the tank fill valve 40, an output for controlling the tank drain valve 30, and an output for controlling a circulation/drain pump 20. Status inputs can be provided for each of the aforementioned control components as well. Additionally, inputs for entering and leaving air temperature and humidity, outdoor air temperature and humidity, tank water level, tank water temperature (which can serve as a proxy for entering and leaving air wet bulb temperatures), and an airflow switch (or a fan status input signal) may be provided as well. The controller 500 can also include the necessary inputs and outputs for desirable operation of the remaining components of the air handling system 1, for example, inputs and outputs to operate the fan 5, damper section 6, and the coils 8, 9.

In one aspect, the controller 500 may be programmed to operate with a demand based control algorithm that activates and deactivates the media stages as necessary to satisfy a cooling demand. By use of the term "demand based" it is meant to include any algorithm which selectively activates and deactivates stages or groups of stages to meet a current output demand setting or load of the system 1. For example, a demand based algorithm could be an algorithm that activates and deactivates the stages to satisfy a temperature set point or relative humidity set point for the air leaving the system 1 via fan 5. It is noted that a single pump serving individual valves associated with each stage may be provided, wherein valves replace pumps 3A, 3B, 3C. The valves may be either modulating valves or two-position type control valves, depending upon application.

Staged Dry Out Process Description

Figure 4:
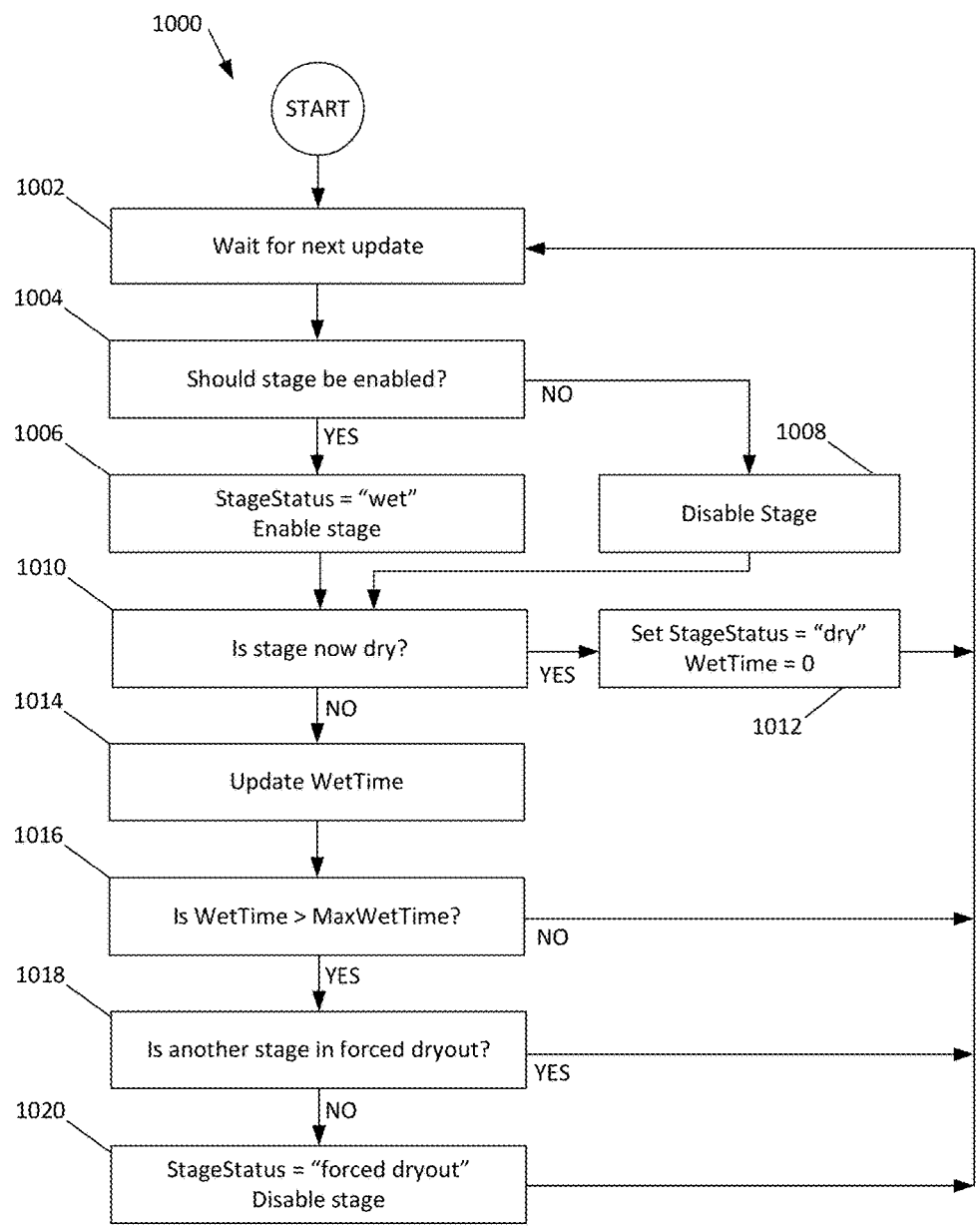
FIG. 4 is a flow diagram for a staged dry out process usable with the evaporative media system shown in FIG. 1 and executable by the control system shown in FIG. 2.

Referring to FIG. 4, an example of a staged dry out process 1000 in accordance with the disclosure is presented. Staged dry out process 1000 operates to eliminate or greatly minimize system shut downs due to dry out requirements, minimizes interruptions in desired system output, and better ensures acceptable system output during required dry out periods.

It is noted that although the figures diagrammatically show steps in a particular order, the described procedures are not necessarily intended to be limited to being performed in the shown order. Rather at least some of the shown steps may be performed in an overlapping manner, in a different order and/or simultaneously. It is also noted, that the described process steps can be performed with respect to individual media stages or with media stages placed in groups (e.g. pairs or larger groups), which may or may not include the same number of media stages. Furthermore, the process shown in FIG. 4 is exemplary in nature and other steps or combinations of steps may be incorporated or altered without departing from the central concepts disclosed herein.

In one aspect, the algorithm is started or initialized, for example when the system is enabled, and includes an update block 1002 wherein the status updates are received. In a step 1004, an evaluation is determined as to whether the stage should be enabled. Where the stage should not be enabled, for example, when the stage is locked out in a forced drying mode or is otherwise unavailable or not needed, the algorithm proceeds to step 1008 where the stage is moved to a disabled state or held in a disabled state. Where the stage should be enabled, the system enables the stage and sets the status of the stage, StageStatus equal to "wet" at a step 1006. Additionally, once the StageStatus changes from "dry" to "wet" a wet timer, WetTime, is initiated at step 1010 to track the duration for which the media stage has been in a non-dry state according to the selected parameters utilized for the determination at step 1010.

In a step 1010, it is determined whether the condition of the media stage is in a dry state. The determination as to whether the media stage is in a dry condition or state can be accomplished with a variety of approaches, for example, by comparing the entering and leaving air temperatures through the media stage. Dry out times can be determined in at least two ways. For example, when the change in temperature between the incoming air and outgoing air through a particular stage are the same (+/−3 degrees), the media stage can be considered to be dry. Alternatively, the media stage can be considered to be dry after a specified amount of time with no addition of water (2 hours), which would equate to the status of the media stage not being in a "wet" condition for at least the specified period of time.

If the media stage is assessed to be in a dry condition at step 1010, a step 1012 is implemented in which the status of the media stage, StageStatus, is set to "dry" and the wet timer, WetTime, is set to zero. Subsequently, the process returns to step 1002 for that media stage. If the media stage is assessed to be in a wet condition at step 1010, the wet condition timer is updated at step 1014.

At a step 1016, the current wet timer value, WetTime, is compared against a maximum wet time value, MaxWetTime. In one example, the maximum wet time value is set to 24 hours. If the timer has not reached the maximum wet time value, the process simply returns to steps 1002 and 1004 for an evaluation as to whether the media stage should be enabled. As long as the stage is and should be enabled and the wet condition timer, WetTime, has not reached the maximum wet time value, MaxWetTime, the process will loop through steps 1002-1006, 1010, 1014, and 1016.

Once the wet condition timer, WetTime, for a media stage has reached or exceeded the maximum wet time value with the stage enabled, the process moves to step 1018. At step 1018, it is evaluated whether any other stage has been locked out of operation. By use of the term "locked out" it is meant to include any condition in which the associated control valve and/or pump for the media stage being evaluated is prevented by the control system from operating in the normal sequencing of the system such that it is not possible for the media stage to be wetted with water and is allowed to dry out. If another media stage is locked out of operation, then the process returns to steps 1002 and 1004 for continued monitoring of the media stage activation status and continued running of the wet condition timer. As long as the stage is activated, the wet condition timer is at or beyond the maximum time period, and another stage is locked out, the process will loop through steps 1002-1006, 1010, and 1014-1018.

If no other media stage is locked out, or once no other media stage is locked out, the process is allowed to move to step 1020 wherein the status for the media stage is set to "forced dryout" and the media stage is locked out from operation. The "forced dryout" status is an indication that the media stage is being forced to dry out to a dry condition because the stage has been active with a "wet" status for at least the maximum time value. With reference to the evaluation at step 1018 regarding whether another stage is in a "forced dryout" condition, the determination at step 1018 may alternatively evaluate the status of the other media stages to determine if any other media stage is in a "locked out" condition. In either case, the process could easily be modified to allow more than one media stage to be in a "forced drying" condition. For example, step 1018 could determine whether a maximum number of other media stages are in the "forced dryout" mode. Alternatively, step 1018 could be eliminated such that every media stage could be placed in the "forced dryout" mode.

Once the media stage has been placed in the forced dryout mode at step 1020, the media stage remains disabled until the media stage has been in the forced dryout mode for a predetermined period of time or until the stage has attained a dry condition in the same manner as at step 1010. In one example, once the locked out stage has reached a dry state or a predetermined time period has expired, the status of the media stage is set to "dry" and the wet condition timer for that stage is stopped and reset to zero, similar to the actions at step 1012. Once the forced dryout mode has concluded, the media stage is unlocked and the process can return back to step 1002 for that stage.

In practice, the algorithm 1000 allows for disabled stages that are not needed to meet the system demand to be monitored as they transition from the wet state to the dry state. These disabled stages can be characterized as being in a "demand based drying" mode, wherein such status is an indication that the media stage is not needed at that time to maintain the desired output of the evaporative media system, and is thus inactive or offline for that reason. As the control loop for each stage continually passes through step 1010, the stage(s) in the demand based drying mode are evaluated for whether the media stage(s) has attained a dry condition, thereby avoiding the need to lock out the stage(s) in the forced dryout mode.

The above described process 1000, ensures that the evaporative media system will never be forced into a zero output condition to fulfill a dry out requirement, unless desired. Rather, only one stage (or a selected number of stages) is permitted to go through a forced dry out cycle at any given time. If one media stage reaches the maximum wet time period while another is in a forced dry out cycle, it will continue operation until a time when it will be the only stage in a forced dry out cycle. While required dry out cycles are being fulfilled, the system will continue to operate with the remaining stages by turning on the minimum number of stages needed to meet or exceed the demand. If demand cannot be met, all remaining unlocked stages will remain turned on. It is also possible that the cyclical demand cycle (e.g. system load) is such that none of the media stages must be placed into a "forced drying" status. During such times, system output will not be interrupted as long as this appropriate cyclical demand cycle continues.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

What is claimed is:

1. A staged dry out process for an evaporative media cooling system comprising a plurality of media stages that are selectively activated and deactivated by a control system, the staged dry out process including the steps of:
   a. monitoring the condition of each media stage to determine whether the media stage is in a wet state or a dry state;
   b. starting a wet condition timer for each stage that is in a wet state;
   c. monitoring whether each media stage is activated or deactivated by the control system;
   d. for any deactivated media stage:
      i. assigning a demand based drying status to the media stage as long as the media stage is in a wet state;
      ii. assigning a dry status to the media stage if or when the media stage reaches a dry state;
   e. for any activated media stage that has not been in a wet state for greater than a maximum predefined time period:
      i. assigning a wet status to the media stage; and
   f. for any activated media stage that has been in a wet state for greater than a maximum predefined time period:
      i. locking out the media stage from activation by the control system until the media stage has reached a dry state;
      ii. assigning a dry status to the media stage.

2. The staged dry out process of claim 1, wherein the step of locking out the media stage from activation by the control system includes allowing only one media stage to be locked at the same time.

3. The staged dry out process of claim 1, wherein the maximum time period is set to 24 hours.

4. The staged dry out process of claim 1, wherein the evaporative media system is a direct evaporative cooler.

5. The staged dry out process of claim 1, wherein the control system is a demand based control system that sequentially activates and deactivates media stages as required to meet an output demand setting.

6. The staged dry out process of claim 1, wherein each media stage includes a plurality of grouped media stages.

7. A staged dry out process for an evaporative media cooling system comprising a plurality of media stages that are selectively activated and deactivated by a control system, the staged dry out process including the steps of:
   a. monitoring the condition of each media stage to determine whether the media stage is in a wet state or a dry state;
   b. starting a wet condition timer for each stage that is in a wet state;
   c. monitoring whether each media stage is activated or deactivated by the control system;
   d. for any activated media stage that has been in a wet state for greater than a maximum predefined time period:
      i. locking out the media stage from activation by the control system until the media stage has reached a dry state;
      ii. assigning a dry status to the media stage.

8. The staged dry out process of claim 7, further including the steps of:
   a. for any deactivated media stage:
      i. assigning a demand based drying status to the media stage as long as the media stage is in a wet state; and
      ii. assigning a dry status to the media stage if or when the media stage reaches a dry state.

9. The staged dry out process of claim 8, further including the steps of:
   a. for any activated media stage that has not been in a wet state for greater than a maximum predefined time period:
      i. assigning a wet status to the media stage.

10. The staged dry out process of claim 7, wherein the step of locking out the media stage from activation by the control system includes allowing only one media stage to be locked at the same time.

11. The staged dry out process of claim 7, wherein the maximum time period is set to 24 hours.

12. The staged dry out process of claim 7, wherein the evaporative media system is a direct evaporative cooler.

13. The staged dry out process of claim 7, wherein the control system is a demand based control system that sequentially activates and deactivates media stages as required to meet an output demand setting.

14. The staged dry out process of claim 7, wherein each media stage includes a plurality of grouped media stages.

15. A control system for an evaporative media cooling system comprising a plurality of media stage, the control system comprising:
   a. a controller having a processor and a non-transient storage medium or memory configured to activate and deactivate each of the plurality of media stages to meet an output demand setting;
   b. the controller being further configured to implement a staged dry out control sequence for each media stage including the steps of:
      i. monitoring the condition of each media stage to determine whether the media stage is in a wet state or a dry state;
      ii. starting a wet condition timer for each stage that is in a wet state;
      iii. monitoring whether each media stage is activated or deactivated by the control system;
      iv. for any activated media stage that has been in a wet state for greater than a maximum predefined time period:
         1. locking out the media stage from activation by the control system until the media stage has reached a dry state;
         2. assigning a dry status to the media stage.

16. The control system of claim 15, wherein the controller is further configured with a control sequence including the steps of:
   a. for any deactivated media stage:
      i. assigning a demand based drying status to the media stage as long as the media stage is in a wet state; and
      ii. assigning a dry status to the media stage if or when the media stage reaches a dry state.

17. The control system of claim 16, wherein the controller is further configured with a control sequence including the steps of:
   a. for any activated media stage that has not been in a wet state for greater than a maximum predefined time period:
      i. assigning a wet status to the media stage.

18. The control system of claim 16, wherein the controller is configured to allow only one media stage to be locked at the same time.

19. The control system of claim 16, wherein the maximum time period is set to 24 hours.

20. The control system of claim 16, wherein the evaporative media system is a direct evaporative cooler.

* * * * *